(12) United States Patent
Schöb (10) Patent No.: US 6,171,078 B1
(45) Date of Patent: Jan. 9, 2001

(54) CENTRIFUGAL PUMP (75) Inventor: Reto Schöb, Volketswil (CH)

(73) Assignees: Sulzer Electronics AG, Winterthur (CH); Lust Antriebstechnik GmbH, Lahnau (DE)

(*) Notice: Under 35 U.S.C. 154(b), the term of this patent shall be extended for 0 days.

(21) Appl. No.: 09/134,187

(22) Filed: Aug. 14, 1998

(30) Foreign Application Priority Data

Sep. 4, 1997 (EP) .................................................. 97810629

(51) Int. Cl.$^7$ ...................................................... F04B 17/00
(52) U.S. Cl. .......................................... 417/423.1; 417/420
(58) Field of Search .............................. 417/423.1, 420, 417/423.12, 423.7, 356; 600/16; 3/1.7; 415/113, 206; 126/634

(56) References Cited

U.S. PATENT DOCUMENTS

| | | | |
|---|---|---|---|
| 3,647,324 | * 3/1972 | Rafferty et al. | 417/420 |
| 4,135,253 | * 1/1979 | Reich et al. | 3/1.7 |
| 5,017,103 | * 5/1991 | Dahl | 417/420 |
| 5,195,877 | * 3/1993 | Kletschka | 417/356 |
| 5,405,251 | * 4/1995 | Sipin | 417/420 |
| 5,499,902 | * 3/1996 | Rockwood | 415/113 |
| 5,683,231 | * 11/1997 | Nakazawa et al. | 417/420 |
| 5,713,730 | * 2/1998 | Nose et al. | 417/423.12 |
| 5,769,069 | * 6/1998 | Caffell | 126/634 |
| 5,803,720 | * 8/1998 | Ohara et al. | 417/420 |
| 5,863,179 | * 1/1999 | Westphal et al. | 415/206 |
| 5,928,131 | * 7/1999 | Prem | 600/16 |
| 5,938,412 | * 8/1999 | Izraelev | 417/423.7 |

\* cited by examiner

Primary Examiner—Teresa Walberg
Assistant Examiner—Leonid Fastovsky
(74) Attorney, Agent, or Firm—Townsend and Townsend and Crew LLP (57) ABSTRACT

A centrifugal pump for delivering a fluid, especially for delivering blood, has a pump housing (2) that has an inlet (3) and an outlet (4) for the fluid, as well as an impeller (5) located inside pump housing (2), said impeller having a plurality of vanes (51) and being rotatable around a rotational axis (A), as well as means for driving impeller (5). Outlet (4) is located offset in the axial direction with respect to impeller (5).

19 Claims, 6 Drawing Sheets

CENTRIFUGAL PUMP

The invention relates to a centrifugal pump for delivering a fluid and in particular to a centrifugal pump for delivering blood, especially a centrifugal pump in which the impeller is magnetically mounted and driven by a rotating field.

WO-A-96/31934 teaches a rotary pump in which the impeller is mounted to float inside the pump housing, supported by magnetic forces, and is driven by a rotating field created by a stator located outside the pump housing. Pumps of this kind are especially advantageous for applications in which the fluid to be delivered must not be contaminated, for example for delivering biological fluids such as blood or highly purified fluids such as super-clean water. In addition, rotary pumps of this kind are suitable for delivering aggressive fluids which would destroy mechanical bearings in a short time.

In designing such rotary pumps as centrifugal pumps, the problem arises that the end turns of the stator and the outlet of the pump housing block the space. To solve this problem, a pump with a so-called "temple" motor has been proposed in WO-A-96/31934 (see FIG. 12 for example) in which the coil cores of the stator each have the shape of an "L" with the long leg in each case running parallel to the rotational axis, while the short leg is directed radially inward toward the rotational axis. The stator, designed as a bearing and drive stator, has two windings, namely the drive winding and the control winding, made in the form of discrete coils and wound around the long legs of the L-shaped coil cores. A temple motor of this kind does not require end turns so that the outlet of the pump housing can be located at the impeller without blocking the space. This design in the form of a temple motor is however subject to the limitation that it has a relatively large space requirement and is relatively expensive.

SUMMARY OF THE INVENTION

It is an object of the present invention to provide a centrifugal pump with a very compact design and with a high output. The centrifugal pump is intended to be as inexpensive as possible and in particular must permit a design in which the impeller is magnetically mounted and can be driven by an electromagnetic rotating field. In particular, a goal of the invention is a centrifugal pump that is as compact and efficient as possible and can be operated using the principle of the bearingless motor.

The invention will now be described in greater detail with reference to embodiments and to the drawing. In the drawings, which are not to scale, identical parts or parts with equivalent functions have been given the same reference numbers, the following are shown.

DESCRIPTION OF THE PREFERRED EMBODIMENTS

The centrifugal pump according to the invention for delivering a fluid, especially blood, has a pump housing 2 (FIG. 1) that has an inlet 3 as well as an outlet 4 for the fluid, as well as an impeller 5 located inside pump hosing 2, said impeller having several vanes 51 and being rotatable around a rotational axis A. Means for driving impeller 5 are also provided. In the centrifugal pump according to the invention, an outlet 4 is offset in the axial direction relative to a radial pressure fluid discharge end of impeller 5.

The term "centrifugal pumps" refers to those rotational or centrifugal pumps in which the fluid to be delivered flows in the direction of the rotational axis A to the impeller, and leaves pump housing 2 in a radial or tangential direction.

In an especially preferred embodiment of the centrifugal pump according to the invention, impeller 5 is mounted magnetically with zero contact in pump housing 2 and driven by an electromagnetic rotating field.

The means for driving the impeller comprise a passive magnetically effective rotor 52 which is part of impeller 5, as well as a stator 6 surrounding pump housing 2, said stator having electrical windings 61. Stator 6 is preferably designed as a bearing and drive stator so that impeller 5 in the operating state is drivable by the magnetic interaction between stator 6 and rotor 52 and can be mounted with zero contact in pump housing 2. Preferably, stator 6 and rotor 52 form a so-called bearingless motor which can be designed in a manner similar to that shown in WO-A96/31934 and especially in international application PCT/CH 96/00335. The functions of the drive and magnetic bearings of rotor 52 are described in detail in these two publications, whose content is incorporated into this description and will therefore not be described in greater detail here.

In the following, the most important features of the principle of the bearingless motor will be summarized briefly. The term "bearingless motor" refers to an electrically controllable bearing and drive device that comprises stator 6 and rotor 52. The term "bearingless motor" is intended to state that stator 6 is simultaneously a driving stator and a bearing stator, in other words no separate stator (and no separate rotor) is provided for the magnetic bearing. Stator 6 is designed and provided with electrical windings 61 so that it generates an electromagnetic rotating field that exerts a torque on rotor 52 so that it rotates around rotational axis A, said field also exerting an arbitrarily adjustable transverse force on the rotor so that its position relative to a plane perpendicular to rotational axis A can be preset or actively controlled. Thus rotor 52 is actively controllable or drivable in the operating state by means of electrical windings 61 of stator 6 with respect to three degrees of freedom, namely its rotation around rotational axis A and its position relative to the plane perpendicular to rotational axis A (two degrees of freedom). For this purpose, electrical windings 61 of stator 6 include for example a drive winding with a pole pair number p and a control winding with a pole pair number p+1 or p−1.

With respect to three additional degrees of freedom, namely tilting relative to the plane perpendicular to rotational axis A (two degrees of freedom) and axial position, rotor 52 is preferably mounted in a magnetically passive manner by reluctance forces, in other words so that it cannot be controlled. For this purpose, stator 6 for example has a plurality of teeth extending radially inward (not shown). For further details of the design and control of stator 6 and/or the design of rotor 52, reference is made here to WO-A-96/31934 and especially to international application PCT/CH 96/00335. The explanations therein regarding drive and mounting can be used similarly for the centrifugal pump according to the invention.

Figure 1:
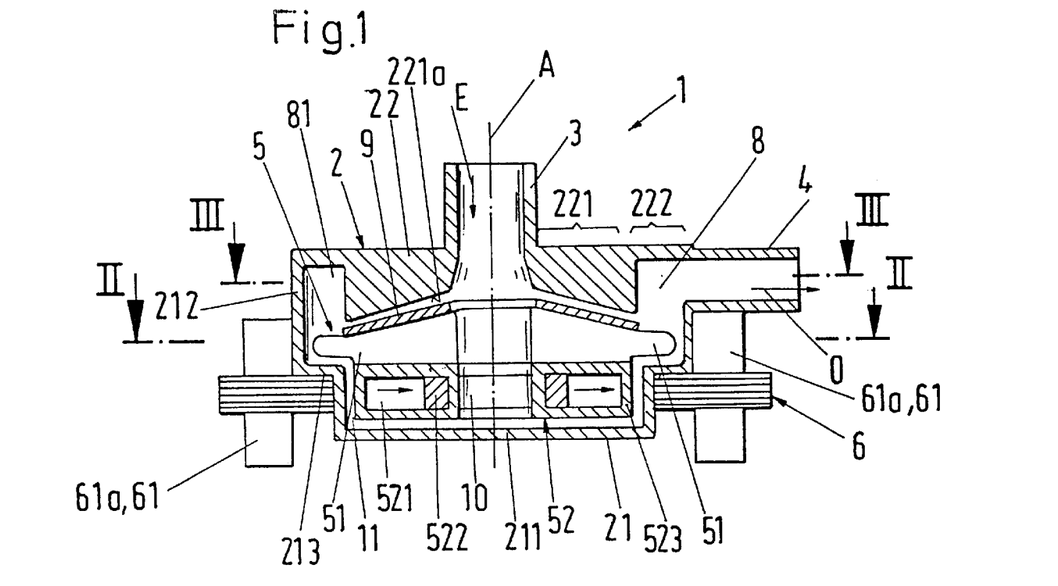
FIG. 1 shows a lengthwise section through a first embodiment of a centrifugal pump made according to the invention.

FIG. 1 shows, in a lengthwise section, a first embodiment of the centrifugal pump according to the invention, designated as a whole by reference number 1. For improved understanding, FIGS. 2 and 3 each show this embodiment in a cross-sectional view along section line II—II (FIG. 2) or along section line III—III in FIG. 1. Pump housing 2 comprises a housing cover 22 as well as a housing part 21 that can be connected together with a hermetic seal. Inlet 3 is designed as an axial inlet through which the fluid to be delivered enters pump housing 2, as indicated by arrow E. Outlet 4 is designed as a tangential outlet through which the fluid leaves pump housing 2 as indicated by arrow O. Inlet 3 and outlet 4 are connected with lines or hoses, not shown, for the fluid. Impeller 5 is located inside pump housing 2, said impeller comprising rotor 52 in the shape of a disc or ring, as well as a plurality of vanes 51 mounted on rotor 52, said vanes preferably being made of plastic. For reasons of improved clarity, only two of the vanes are shown in FIG. 1. In the operating state, impeller 3 rotates around rotational axis A. Pump housing 2 is surrounded by bearing and drive stator 6 with electrical windings 61. Electrical windings 61 are shown in the form of end turns 61a. Rotor 52 in the shape of a ring comprises an annular permanent magnet 521, an iron return 522 located coaxially and radially internally with respect thereto, as well as jacket 523, preferably made of titanium or plastic. Vanes 51 are connected nonrotationally with jacket 523. Permanent magnet 521 is magnetized diametrically as shown by the two arrows without reference numbers for example. The passive magnetically effective rotor 52, together with stator 61 and supply and control devices, not shown, comprises a bearingless motor 52 that is actively controllable and/or drivable with respect to its rotation around axis A and its position in the plane perpendicular to rotational axis A, and is mounted to tilt magnetically passively relative to said plane and to its axial position, under the influence of reluctance forces in stator 6.

As is evident from FIG. 1 in particular, according to the invention, outlet 4 is offset relative to impeller 5 in the axial direction, namely higher as shown in FIG. 1. As a result of this measure, a very simple solution can be found to the design problems that result from the fact that in the centrifugal pump, outlet 4 must pass the end turns 61a of stator 6. Outlet 4, as shown in FIG. 1, is provided above end turns 61a so that there is no interference between outlet 4 and end turns 61a. For reasons of compactness, outlet 4 is preferably located immediately above end turns 61a and in particular rests on them. In comparison to the temple motor mentioned at the outset, the arrangement of outlet 4 according to the invention has the advantage of permitting a design of centrifugal pump 1 that is definitely shorter in the axial direction and hence the pump can be made much more compact.

Housing part 21 forms the essentially flat bottom 211 of pump housing 2 as well as its side wall 212. A housing recess 213 is provided in side wall 212 at which pump housing 2 expands in the radial direction. Housing cover 22 has a central area 221 whose inner boundary surface 221a facing impeller 5 is made conical and extends in the radial direction for approximately the same distance as bottom 211. Central area 221 is abutted in the radial direction by an essentially annular area 222 that extends up to side wall 212 and whose axial thickness is less than that of central area 221. Thus, pump housing 2 has a guide channel that is essentially annular and extends in the circumferential direction of pump housing 2, said guide channel connecting inlet 3 with outlet 4. Guide channel 8 is delimited by housing recess 213, side wall 212, the wall of annular area 222, and the lateral boundary of central area 221. Guide channel 8 thus comprises a partial chamber 81 which, viewed in the axial direction, is offset relative to impeller 5, said partial chamber surrounding central area 221 of housing 221 in the circumferential direction and being located above the radial outer ends of vanes 51 as shown in FIG. 1. This design of guide channel 8 can be described, pictorially speaking, in such fashion that the guide channel, which in conventional centrifugal pumps is located symmetrically with respect to the outer ends of the vanes, is "folded" in the axial direction, i.e. upward in FIG. 1.

Since this results in guide channel 8, by virtue of axially offset partial chamber 81, having sufficient volume for the fluid to be delivered, vanes 51 of impeller 5 can be designed as an additional advantageous measure such that they extend into guide channel 8, as viewed in the radial direction. By virtue of this measure, the effective vane length increases, so that the efficiency, especially the delivery efficiency, of centrifugal pump 1 can be increased even further without increasing the external dimensions of centrifugal pump 1. This design of vanes 51 which project in the radial direction beyond rotor 52, by 15–20% of its diameter for example, can be clearly seen in FIGS. 2 and 3.

Figure 3:
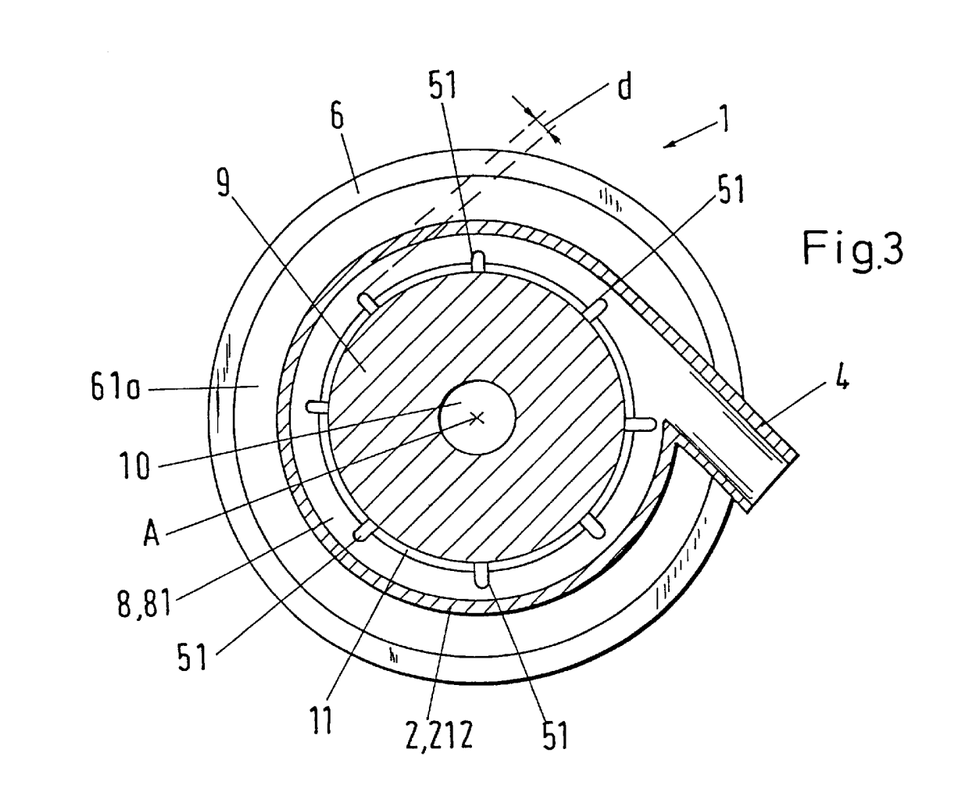
FIG. 3 shows a cross section through the first embodiment along section line III—III in FIG. 1.

As can be seen best from the cross-sectional view in FIG. 3, guide channel 8 in this embodiment is designed as an annular chamber, in other words with a cross section that remains essentially constant around its circumference so that all of the radially outer ends of vanes 51 essentially have the same spacing d from side wall 212 of pump housing 2 in the normal operating state.

In the axial direction, a likewise conical cover plate 9 (see also FIG. 1) can be located between vanes 51 of impeller 5 and housing cover 22 of pump housing 2, especially the conical boundary surface 221a of central area 221 of housing cover 22, mounted for example on vanes 51 in order to reduce the backflow of the fluid from guide channel 8 toward inlet 3. Cover plate 9 extends in the radial direction approximately as far as the radially inner limit of guide channel 8, in other words the lateral boundary of central area 221 of housing cover 22, so that vanes 51, as viewed in the radial direction, project beyond the end of the cover plate.

Figure 2:
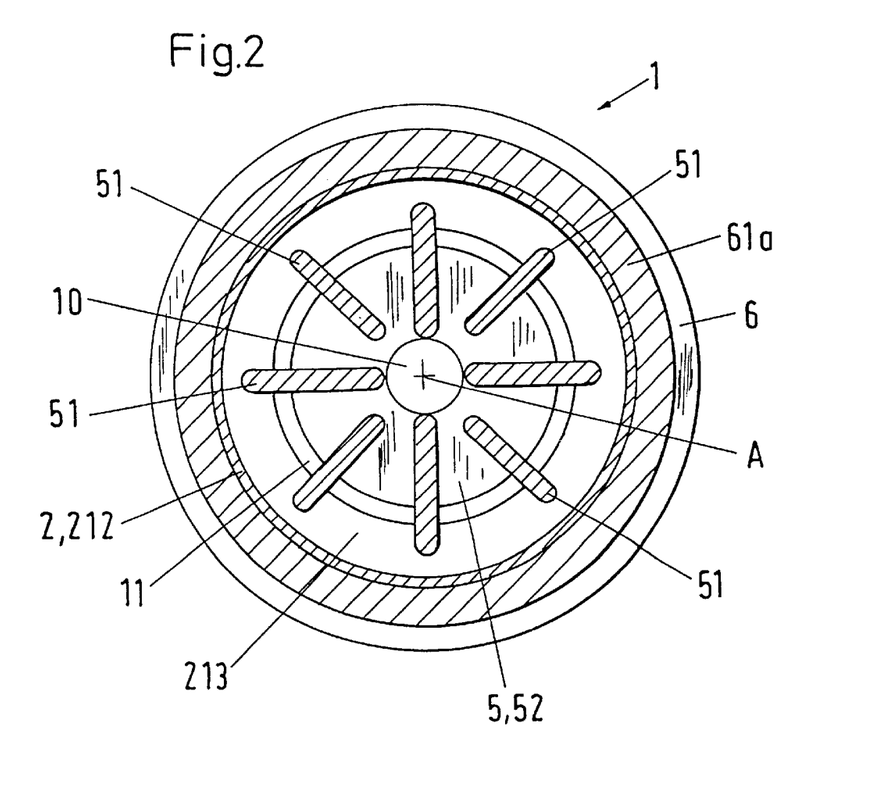
FIG. 2 is a cross section through the first embodiment along section line II—II in FIG. 1.

The center hole in annular rotor 52 in the embodiment according to FIGS. 1–3 constitutes a through relief bore 10 of impeller 5 in its axial area. In the operating state of centrifugal pump 1, fluid can pass through gap 11 between impeller 5 and side wall 212 into the chamber between bottom 211 and the end of rotor 52 facing it, and from there can pass in the axial direction through relief bore 10, flowing backward. By appropriate dimensioning of gap 11 and relief bore 10, hydrodynamic compensation of axial thrust can be achieved to compensate at least partially for the forces acting upward in the axial direction on impeller 5 as shown in FIG. 1. As a result of this measure, the passive magnetic axial bearing of impeller 5 is sufficient, especially even at high output levels.

In the operating state, impeller 5 rotates around rotational axis A, driven and suspended by the magnetic interaction between rotor 52 and bearing and drive stator 6. The fluid to be delivered moves in the axial direction through inlet 3, is accelerated by vanes 51 in an essentially radial direction, and is delivered into guide channel 8 where it is initially deflected in the axial direction and then leaves the guide channel through outlet 4 in the tangential direction. At least one flow component then prevails in guide channel 8 that is directed opposite to the flow in the vicinity of inlet 3.

Figure 4:
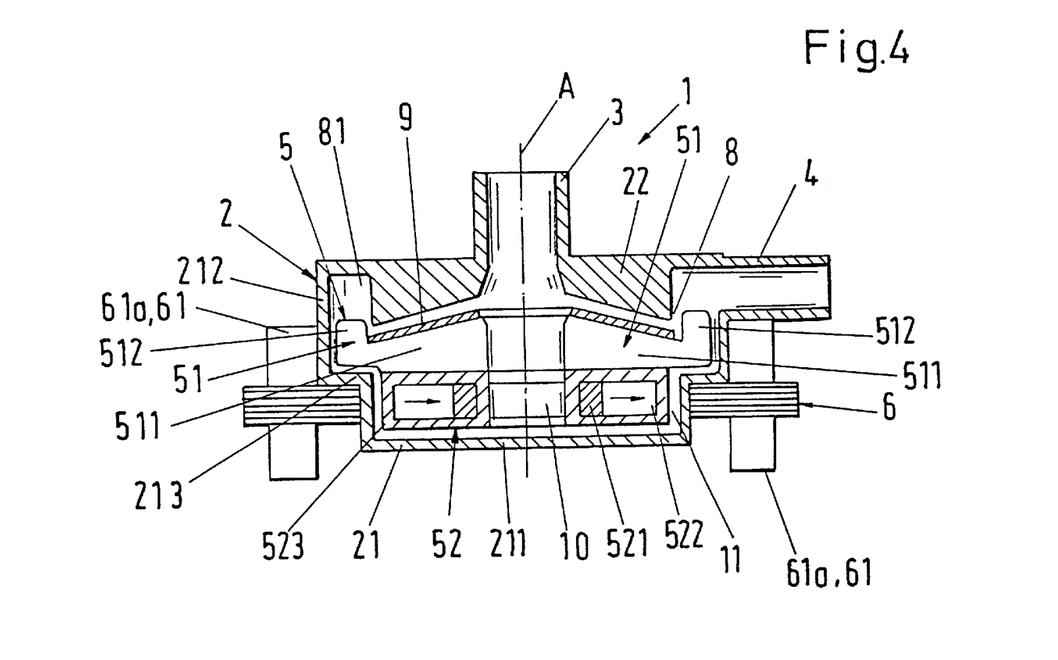
FIG. 4 is a lengthwise section through an improvement to the first embodiment.

FIG. 4 shows a lengthwise section through an improvement on the first embodiment. Here again, for reasons of improved clarity, only two of vanes 51 are shown. In this improvement, vanes 51 of impeller 5 are each angled so that each has a radial part 511 that extends outward in a straight line or is curved in the radial direction, as well as an axial part 512 adjacent thereto, said part extending essentially parallel to rotational axis A of impeller 5 or parallel to side wall 212 of pump housing 2. Axial part 512 extends up to partial chamber 81 of guide channel 8. Vanes 51 therefore are each "folded" in the axial direction, i.e. upward as shown in FIG. 4. As a result of this advantageous measure, the effective vane length is increased even further, so that the efficiency, especially the output, of the centrifugal pump can be increased further without the outer dimensions of the centrifugal pump increasing. In particular, the folded design of vanes 51 means that the fluid is guided longer by vanes 51 and the pressure of the fluid can be increased as a result.

Figure 5:
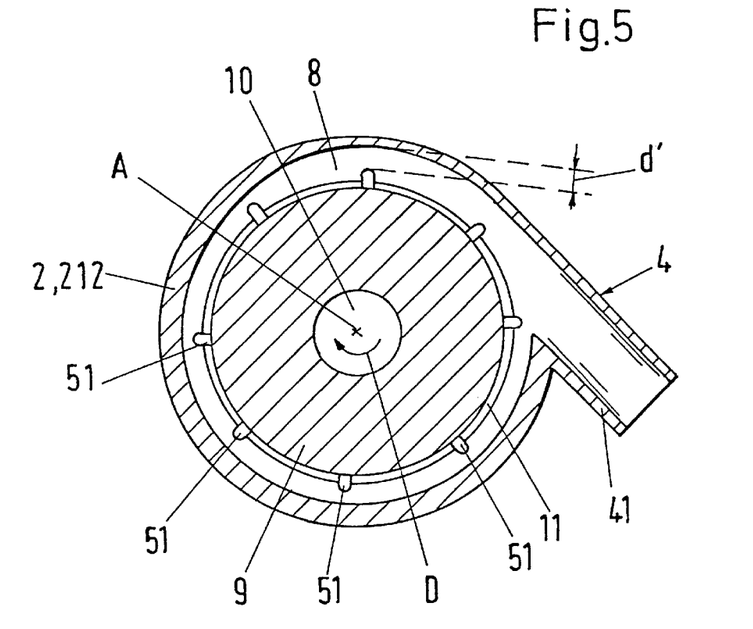
FIG. 5 is a cross section similar to FIG. 3 of a variation on the design of the guide channel (stator and electrical windings not shown)

FIG. 5 shows a variation on the design of guide channel 8. FIG. 5 corresponds to the view in FIG. 3, i.e. a cross section along section line III—III in FIG. 1. The design of stator 6 and electrical windings 61 will be omitted from FIG. 5 however because they are designed similarly to those in FIG. 3.

In this version according to FIG. 5, guide channel 8 is designed in the radial direction as a helical chamber so that space d' between the radially outer ends of vanes 51 and the wall of the pump housing that borders guide channel 8, namely side wall 212, increases as viewed in the rotation direction. The rotation direction is indicated by arrow D in FIG. 5. Space d' is smallest in the vicinity of shorter leg 41 of tangential outlet 4 and then increases as viewed in rotation direction D. This design of guide channel 8 as a radial helical chamber takes into account the fact that the volume of fluid located in the guide channel, as viewed in rotation direction D, increases toward outlet 4. The radial helical chamber for example can be made such that side wall 212 of pump housing 2 has a wall thickness that decreases in the circumferential direction, as can be seen from FIG. 5.

Figure 6:
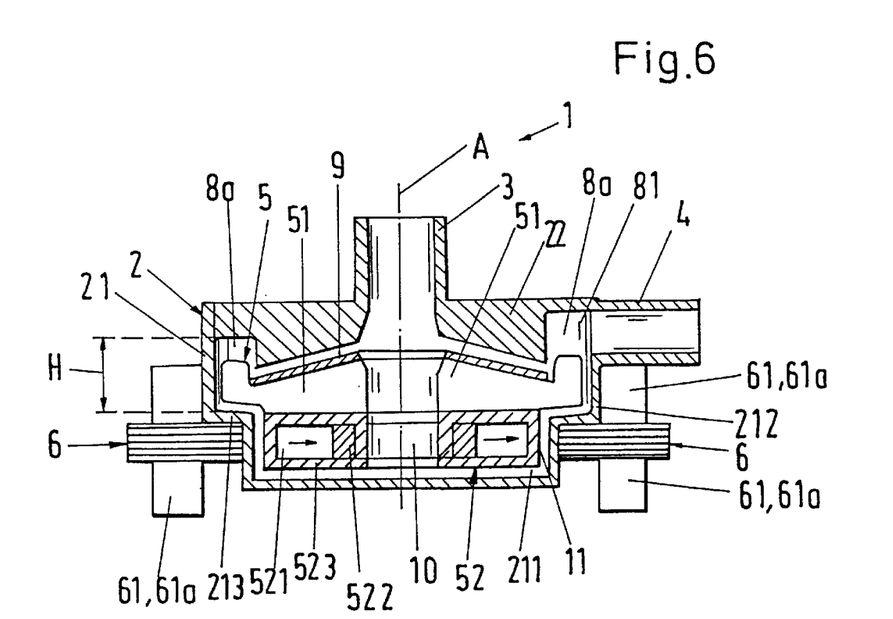
FIG. 6 is a lengthwise section through a second embodiment of the centrifugal pump according to the invention.

FIG. 6 shows a second embodiment of centrifugal pump 1 according to the invention in a lengthwise section. In FIG. 6 as well, for reasons of improved clarity, only two of vanes 51 are shown. The important difference from the first embodiment consists in the design of guide channel 8a, but the explanations of the first embodiment otherwise apply in similar fashion to the second embodiment as well.

Figure 7:
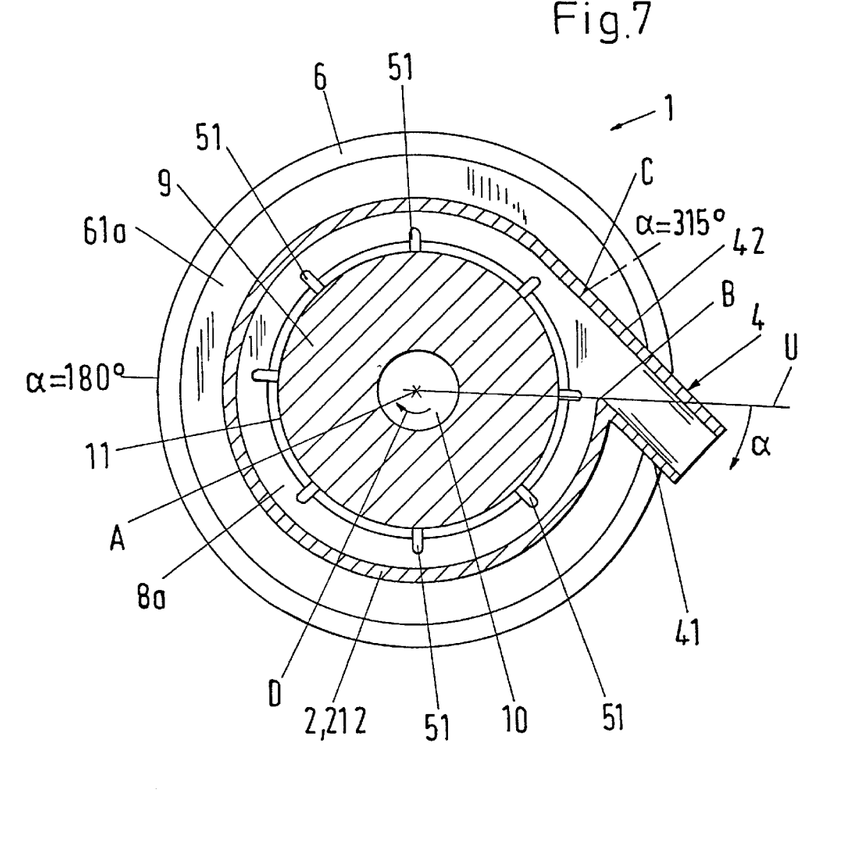
FIG. 7 is a cross section through the second embodiment corresponding to FIG. 3.
Figure 8:
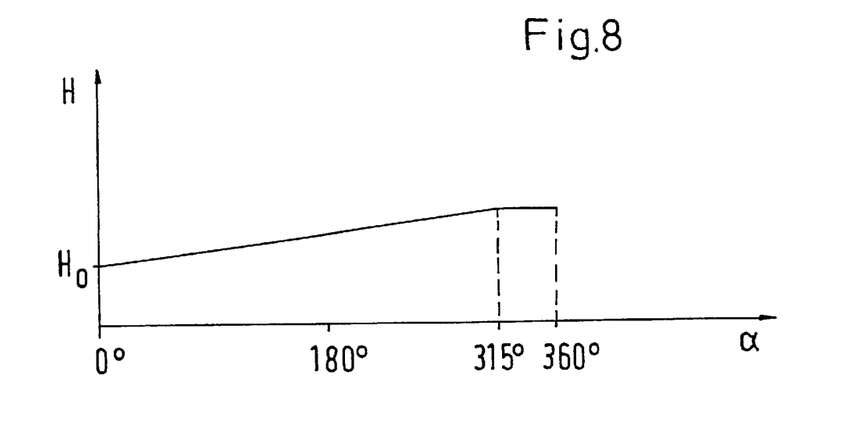
FIG. 8 is a graph showing the axial height of the guide channel as a function of an azimuth angle.

In the second embodiment, axial height H of guide channel 8a increases in the circumferential direction so that guide channel 8a forms an axial helical chamber. This design feature is explained in greater detail in FIG. 7 for example, said figure showing a cross-sectional view corresponding to FIGS. 3 and 5, and in FIG. 8. FIG. 8 shows a graph that represents the axial height H of guide channel 8a as a function of an azimuth angle α. Angle α is determined as follows (see FIG. 7). Angle α is measured from an imaginary connecting line U running radially between rotational axis A and point of application B of shorter leg 41 of tangential outlet 4. This connecting line U therefore corresponds to an angle α=0°. Angle α increases, as viewed in rotation direction D. The point of application C of longer leg 42 of tangential outlet 4 in this specific design for example is α=315°.

FIG. 8 shows the axial height of guide channel 8a as a function of angle α. The axial height H for α=0° has its minimum value $H_0$ and then increases with increasing values of α up to point of application C of longer leg 42 at α=315°. Along outlet 4, in other words for 315°≦α360°, axial height H is constant.

Designing pump housing 8a as an axial helical chamber is especially advantageous from the standpoint of flow technology, especially when combined with angled vanes 51.

Of course, designs are also possible in which guide channel 8; 8a is designed as both a radial and an axial helical chamber, and therefore expands radially as viewed in the circumferential direction while at the same time it has an increasing axial height H.

Figure 9:
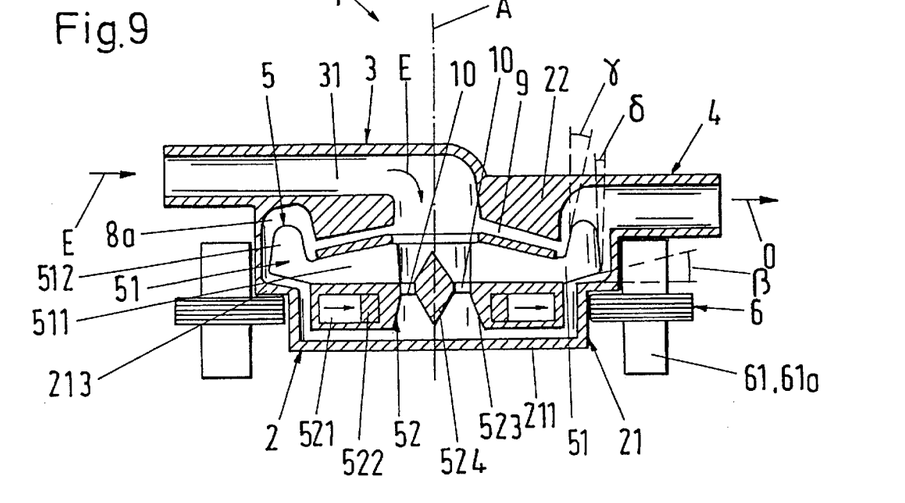
FIG. 9 is a lengthwise section through an improvement on the second embodiment.

In a lengthwise section, FIG. 9 shows an improvement on the second embodiment. In FIG. 9 also, for reasons of improved clarity, only two of vanes 51 are shown. There is an important difference in the design of inlet 3. Inlet 3 in this improvement comprises an angled inlet channel 31 that initially extends essentially radially with respect to rotational axis A, and then curves toward rotational axis A so that the fluid can pass in the axial direction to impeller 5, as indicated by arrows E in FIG. 9. As shown in FIG. 9, the part of inlet channel 31 that runs radially is guided toward rotational axis A from a side other than the side toward which outlet 4 extends. This measure, especially when combined with the design of guide channel 8a as an axial helical chamber, permits an especially compact design for centrifugal pump 1. Since guide channel 8a as shown in FIG. 9 has a smaller axial height H on the left side than on the right side where outlet 4 is located, the part of inlet channel 31 that runs radially with respect to the axial direction can be located closer to impeller 5, especially in such fashion that the part of inlet channel 31 that runs radially and outlet 4 overlap at least partially in their axial positions. Preferably, inlet channel 31 is integrated into pump housing 2. By these measures, centrifugal pump 1 extends as little as possible in the axial direction because of the optimized utilization of the available space, so that the pump is very compact and at the same time permits high efficiency.

Another advantageous measure which can of course be used in an essentially similar fashion for the first embodiment or in its improvement as well, relates to the design of vanes 51 of impeller 5.

As can be seen from FIG. 9, the radially outer ends of vanes 51, on their sides facing away from inlet 3 (according to the diagram in FIG. 9, these are the undersides of vanes 51) are each beveled at an angle β relative to the rotational plane that runs perpendicularly to rotational axis A. As a result, vanes 51 are prevented from striking pump housing 2, especially housing recess 213, when impeller 5 is tilted slightly.

If vanes 51 are designed to be folded, in other words each have an axial part 512, axial parts 512 of vanes 51 are preferably beveled at an angle γ or δ at their radially inner and/or radially outer limits relative to the direction of rotational axis A in order to prevent vanes 51 striking anything during slight tilting movements relative to the rotational plane.

For practical reasons, angles β, γ, and δ of the bevels are each preferably smaller than 10° and especially smaller than 5°. Designs in which all three angles β, γ, and δ have the same value are especially preferred.

Figure 10:
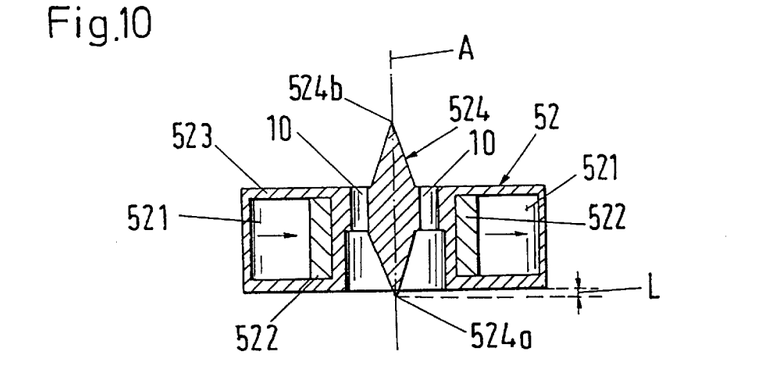
FIG. 10 is a detailed view of the rotor in FIG. 9.

FIG. 9 also shows a likewise preferred version for designing rotor 52 of impeller 5. The detailed view in FIG. 10 makes these variations clear. In contrast to the design described earlier, jacket 523 that surrounds annular permanent magnet 521 as well as iron return 522 has a part 524 in its central area that is in the shape of a double cone, whose two points 524a and 524b both lie on rotational axis A, with one cone of double-cone-shaped part 524 having its point 524b oriented in the direction of inlet 3 and the other cone having its point 524a oriented away from inlet 3 in the direction of housing bottom 211. The first cone serves primarily to guide the flow of the fluid better. The other cone is designed so that its point 524a projects in the axial direction for a distance L beyond the remainder of jacket 523. Consequently, impeller 5, at its end facing away from inlet 3 in the axial direction, has a projecting point 524a by which it can abut bottom 211 of pump housing 2 if necessary. Point 524a thus forms a so-called "backup bearing," which ensures for example that impeller 5 can continue rotating if lowering occurs, particularly as the result of a brief overload on the passive magnetic axial bearing, namely on point 524a, essentially without impediment.

Figure 11:
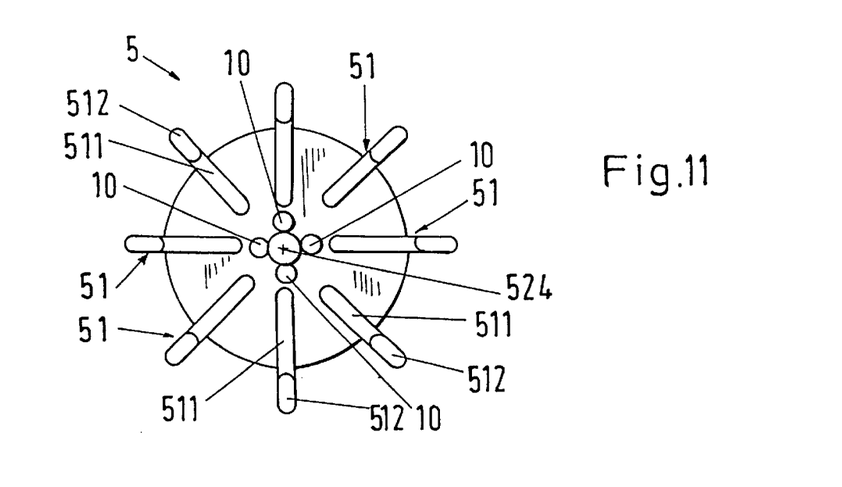
FIG. 11 is a view of the impeller in FIG. 9, as viewed from the inlet in the axial direction (cover plate not shown)

In this design of the rotor, a plurality of relief bores 10 is preferably provided said bores being arranged around double-cone-shaped part 524. This is especially clear from the diagram in FIG. 11, which shows a top view of impeller 5 of centrifugal pump 1 shown in FIG. 9 as viewed from inlet 3. Cover plate 9 is not shown in FIG. 11. In this specific design, four relief bores 10 are provided, distributed uniformly around double-cone-shaped part 524.

Of course the design of rotor 52 or of impeller 5 with double-cone-shaped part 524 is also possible in the first embodiment or its improvement.

Figure 12:
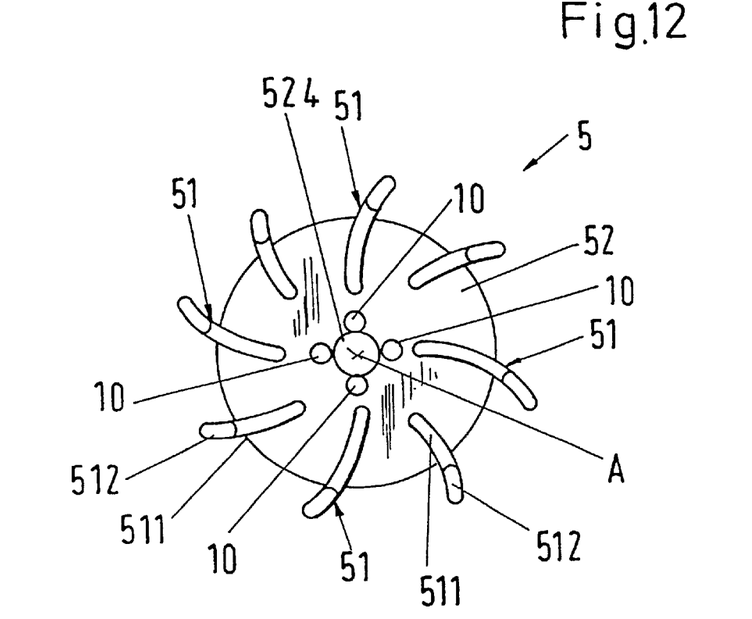
FIG. 12 is a top view of the impeller as viewed from the inlet in the axial direction, with a variation in the vanes (cover plate not shown)
Figure 13:
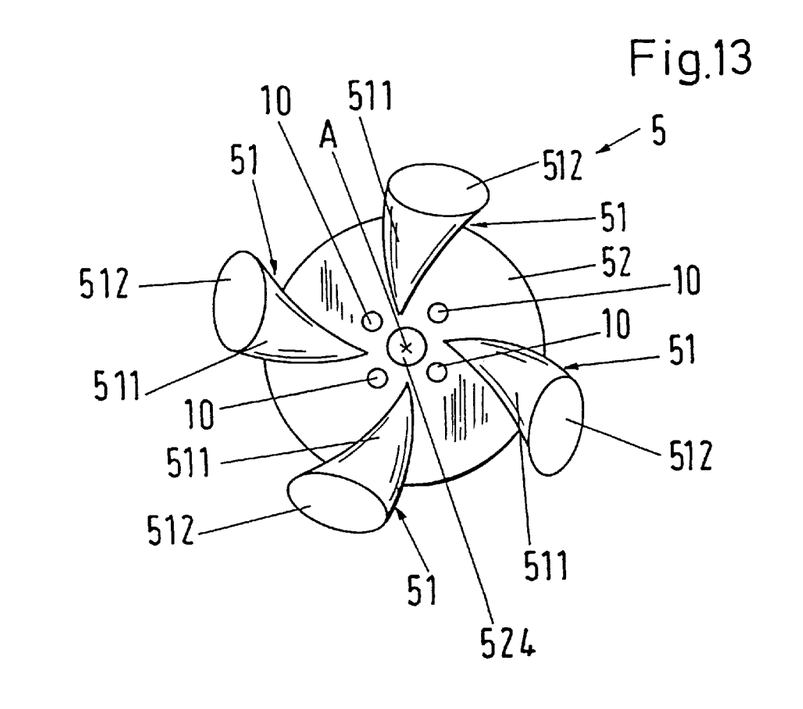
FIG. 13 is a top view of the impeller as viewed from the inlet in the axial direction for another variation in the vanes (cover plate not shown).

Numerous variations are possible in the shape of vanes 51 of the centrifugal pump according to the invention, of which only a few are described here but not by way of a limitation. Vanes 51, as shown in FIG. 2, can be designed for example so that they extend in a straight line in the radial direction. FIGS. 12 and 13, each of which shows a top view of embodiments of impeller 5 (cover plate 9 is not shown), illustrate two further variations on vanes 51. In the embodiment shown in FIG. 12, vanes 51, especially their radial parts 511, follow in a curved path outward relative to the radial direction. Finally, FIG. 13 shows an embodiment in which the thickness of the vanes decreases outward.

Of course the invention is not limited to centrifugal pumps in which the impeller is magnetically mounted and driven by a rotary field. The centrifugal pump according to the invention is especially suited for those applications in which the external shape is subject to limitations like those caused for example by end turns 61a.

The centrifugal pump according to the invention is especially characterized by its high performance combined with an extremely compact design.

In the special design according to the principle of the bearingless motor, with magnetic zero-contact mounting of the impeller and driven by means of a rotary field, the centrifugal pump according to the invention is especially suited for those applications in which strict isolation of the fluid to be delivered from the environment is essential and in which contamination of the fluid (by abrasion in mechanical bearings for example) must be avoided. The centrifugal pump according to the invention is therefore especially suitable for delivering biological or highly pure or aggressive or dangerous substances. The centrifugal pump according to the invention is especially suitable as a blood pump, operated outside or inside a human or animal body, because of its high delivery rate combined with a compact design.

What is claimed is:

1. Centrifugal pump for delivering a fluid comprising a pump housing that has an inlet and an outlet for the fluid, and a guide channel extending in a circumferential direction of the pump housing, an impeller located inside the pump housing having a plurality of vanes and being rotatable about a rotational axis which extends in an axial direction of the pump, and a drive unit for driving the impeller, the outlet being offset in the axial direction relative to the impeller, the guide channel being shaped so that fluid after being accelerated by the vanes first flows in an axial direction and then leaves the guide channel through the outlet.

2. Centrifugal pump according to claim 1, wherein the drive unit comprises a passive magnetically effective rotor that is part of the impeller, and a stator surrounding the pump housing, the stator having electrical windings and functioning as a bearing and drive stator, so that the impeller is driven in the operating state by the magnetic interaction between the stator and the rotor and is mounted with zero contact in the pump housing.

3. Centrifugal pump according to claim 1 wherein the guide channel is essentially annular and comprises a partial chamber that is offset relative to the impeller in the axial direction.

4. Centrifugal pump according to claim 1 wherein the vanes of the impeller extend into the guide channel in a radial direction.

5. Centrifugal pump according to claim 1 including a cover plate located in the axial direction between the vanes of the impeller and a housing cover of the pump housing, said plate extending in a radial direction approximately up to a radially internal boundary of the guide channel.

6. Centrifugal pump according to claim 2 wherein the rotor is controllable and/or drivable in the operating state by means of electrical windings of the stator relative to three degrees or freedom in an active manner, and is mounted magnetically passively in the stator with respect to three additional degrees of freedom by reluctance forces.

7. Centrifugal pump according to claim 1 wherein each vane of the impeller has a radial part that extends outward in a radial direction and an adjoining axial part that extends essentially parallel to the axial direction.

8. Centrifugal pump according to claim 1 wherein the guide channel has a helical chamber extending in a radial direction so that a space between radially outer ends of the vanes and a wall of the pump housing that delimits the guide channel increases as viewed in a rotational direction.

9. Centrifugal pump according to claim 1 wherein an axial height of the guide channel increases in a circumferential direction.

10. Centrifugal pump according to claim 1 wherein the inlet comprises an angled inlet channel that initially extends primarily radially with respect to the rotational axis and then curves in the direction of a rotational axis of the impeller so that the fluid travels to the impeller in the axial direction.

11. Centrifugal pump according to claim 1 wherein radially outer ends of the vanes form sides facing away from the inlet relative to a rotational plane of the impeller and are beveled with respect to the rotational plane at an angle which is smaller than 10°.

12. Centrifugal pump according to claim 7 wherein the vanes have axial parts radially inner and/or radially outer boundaries of which are beveled relative to a rotational axis of the impeller at an angle which is smaller than 10°.

13. Centrifugal pump according to claim 1 wherein the impeller has at least one through relief bore proximate an axis of the impeller.

14. Centrifugal pump according to claim 1 wherein the impeller, at its end facing away from the inlet in the axial direction, has a projecting point for supporting the impeller as needed on a bottom of the pump housing.

15. A centrifugal pump according to claim 7 wherein the radial part extends in a radially outward direction in a straight line.

16. A centrifugal pump according to claim 7 wherein the radial part extends in a radially outward direction along a curved line.

17. A centrifugal pump according to claim 12 wherein the angle is less than 5°.

18. A centrifugal pump according to claim 12 wherein the angle is smaller than 5°.

19. Centrifugal pump for delivering a fluid comprising a pump housing having an inlet and an outlet, and an impeller inside the pump housing rotatable about an axis of rotation which extends in an axial direction of the pump and having a plurality of vanes ends of which define a radial pressurized fluid discharge end of the impeller, the outlet being spaced apart in the axial direction relative to the discharge end of the impeller.

* * * * *